(12) United States Patent
Hasley et al.

(10) Patent No.: US 11,430,563 B2
(45) Date of Patent: Aug. 30, 2022

(54) CONFIGURING AND DISPLAYING A USER INTERFACE WITH HEALTHCARE STUDIES

(71) Applicant: FUJIFILM MEDICAL SYSTEMS U.S.A., INC., Lexington, MA (US)

(72) Inventors: Thomas Hasley, Clayton, NC (US); Keiji Sugihara, Morrisville, NC (US); Brigil Vincent, Morrisville, NC (US); Matthew Andersen, Morrisville, NC (US)

(73) Assignee: FUJIFILM MEDICAL SYSTEMS U.S.A., INC., Lexington, MA (US)

( * ) Notice: Subject to any disclaimer, the term of this patent is extended or adjusted under 35 U.S.C. 154(b) by 0 days.

(21) Appl. No.: 16/198,421

(22) Filed: Nov. 21, 2018

(65) Prior Publication Data

US 2020/0160973 A1 May 21, 2020

(51) Int. Cl.
*G06F 3/048* (2013.01)
*G16H 30/00* (2018.01)
(Continued)

(52) U.S. Cl.
CPC ........... *G16H 30/40* (2018.01); *G06F 3/0482* (2013.01); *G06F 3/04847* (2013.01);
(Continued)

(58) Field of Classification Search
CPC .... G06F 3/048; G06F 3/0482; G06F 3/04847; G16H 30/40; G06T 7/0012; G06T 2200/24; G06T 2207/20092
See application file for complete search history.

(56) References Cited

U.S. PATENT DOCUMENTS 7,844,089 B2 * 11/2010 Kanada .................. G16H 30/20
                                                        382/128
10,799,189 B2 * 10/2020 Nye ....................... A61B 6/032
(Continued)

FOREIGN PATENT DOCUMENTS

WO    2010100610    9/2010
WO    2015055469    4/2015

OTHER PUBLICATIONS

Spanish Search Report for Application No. 201931017 dated Apr. 21, 2020, 11 pages.
(Continued)

*Primary Examiner* — Mahelet Shiberou
(74) *Attorney, Agent, or Firm* — Heslin Rothenberg Farley & Mesiti P.C.

(57) ABSTRACT

A method and apparatus for configuring and displaying a user interface with healthcare studies. In one embodiment, the method comprises accessing user-specified configuration information for configuring a first user interface of a medical image management system, the first user interface to display a list of healthcare studies including one or more unread healthcare studies; and creating the first user interface with the list of healthcare studies with priority information for the one or more unread healthcare studies, including determining the priority information, according to the user-specified configuration information, for at least one unread healthcare study in the list based on findings that result from performing automated image analysis on one or more of the images in said at least one unread healthcare study.

26 Claims, 7 Drawing Sheets

(51) Int. Cl.
 *G16H 30/40* (2018.01)
 *G06F 3/0482* (2013.01)
 *G06T 7/00* (2017.01)
 *G06F 3/04847* (2022.01)

(52) U.S. Cl.
 CPC ........ *G06T 7/0012* (2013.01); *G06T 2200/24* (2013.01); *G06T 2207/20092* (2013.01)

(56) References Cited

U.S. PATENT DOCUMENTS

| | | | |
|---|---|---|---|
| 2007/0041623 A1* | 2/2007 | Roehrig | G16H 50/20 382/128 |
| 2008/0086684 A1 | 4/2008 | Hertel et al. | |
| 2009/0132279 A1* | 5/2009 | Yeluri | G06F 19/321 705/3 |
| 2009/0208076 A1* | 8/2009 | Nakajima | G06F 19/321 382/128 |
| 2011/0077958 A1 | 3/2011 | Breitenstein et al. | |
| 2012/0225384 A1 | 9/2012 | Wang et al. | |
| 2013/0024208 A1* | 1/2013 | Vining | A61B 6/468 705/3 |
| 2013/0039552 A1* | 2/2013 | Becker | G06F 16/51 382/128 |
| 2013/0325510 A1 | 12/2013 | Vendrell | |
| 2014/0358585 A1* | 12/2014 | Reiner | G16H 80/00 705/3 |
| 2016/0350919 A1* | 12/2016 | Steigauf | G06T 7/0014 |
| 2016/0364857 A1 | 12/2016 | Reicher et al. | |
| 2018/0032556 A1 | 2/2018 | Dominick et al. | |
| 2018/0067958 A1* | 3/2018 | Reicher | G16H 10/20 |
| 2018/0137244 A1* | 5/2018 | Sorenson | G16H 30/20 |
| 2019/0156937 A1* | 5/2019 | Shimomura | G16H 50/30 |
| 2019/0228270 A1* | 7/2019 | Deluca | G06F 16/5846 |
| 2019/0340753 A1* | 11/2019 | Brestel | G16H 50/30 |
| 2019/0392944 A1* | 12/2019 | Samset | G06T 7/0012 |

OTHER PUBLICATIONS

United Kingdom Search Report for Application No. GB1915773.4 dated Apr. 1, 2020, 7 pages.
European Examination Report, European Application No. GB1915773. 4, dated Feb. 9, 2022.
Result of the Substantive Examination of the Patent Application for Invention 201931017, Dated Apr. 22, 2022, 6 Pages.

* cited by examiner

Priority Color Column 501

Priority Level 500

Score Column 502

| All Studies Demo - new | | | | | | | | | |
|---|---|---|---|---|---|---|---|---|---|
| 📷 | 📄 | ✎ | 📄 | 🔒 | ⚑ | Priority | ⊚ | ‖△ Score | |
| 📷 | | | 📄 | | | R | ▨ | 85 | |
| 📷 | | | 📄 | | | R | ▨ | 90 | |
| 📷 | | | 📄 | | | R | ▨ | 65 | |
| 📷 | | | 📄 | | | R | ▨ | 70 | |
| 📷 | | | 📄 | | | R | ▨ | 60 | |
| 📷 | | | 📄 | | | R | ▨ | 65 | |

FIG. 5A

- ▨ AI findings and emergency (value: 1, sort order: 1)
- ▨ AI findings but not emergency (value: 2, sort order: 2)
- ▨ No AI findings (value: 3, sort order: 3)
- ▨ AI being processed currently (value: 4, sort order: 1000)
- AI not processed (value: NULL, sort order: 1000)

FIG. 5B

CONFIGURING AND DISPLAYING A USER INTERFACE WITH HEALTHCARE STUDIES

FIELD OF THE INVENTION

Embodiments of the present invention relate to the field of medical imaging; more particularly, embodiments of the present invention relate to configuring and displaying a list of healthcare studies based on findings from automated image analysis.

BACKGROUND

Physicians and other medical personnel often review all of a patient's relevant clinical information when making healthcare decisions. The clinical information is typically included in healthcare studies and structured reports. These often include information about a patient's history, diagnostic reports from different domains, images, and other clinical data in electronic format.

The healthcare studies of a patient include a diagnostic imaging report that contains parameter values (e.g., measurements, readings, etc.) and images from examinations or procedures that are usually shared among physicians and clinicians to help in diagnosis and treatment.

The healthcare studies are typically generated in response to a physician ordering an examination for their patient. The examination is performed and the generated study is often sent to a Picture Archiving and Communication System (PACS). A physician or clinician can use a medical image management system to obtain a worklist containing studies for their patients. Current systems allow users to sort these worklists based on various inputs, many of which are based on a priority level set when a physician orders an examination based on a patient's condition as seen or explained. For example, the priority assigned by the physician may correlate into some common industry terms such as, for example, Routine, STAT, Urgent, etc.

Various Artificial Intelligence (AI) algorithms have recently been utilized with Radiology PACS systems. These algorithms automate the process of evaluating images in the healthcare studies. These algorithms can be applied to single images or complete studies, and the results will be made accessible to the interpreting physician, as well as other clinical users. Even though algorithm results are available, the interpreting physician may be unaware of the findings if the list of studies has been sorted by other methods, which in some cases could include priority as set by the ordering physician. Because the automated findings associated with a procedure does not change priority by itself, then the automated results may appear lower on the list and not reviewed in a timely manner, which could cause a patient more harm or delay in treatment if not reviewed with the quickness associated with the priority level of the findings.

SUMMARY OF THE INVENTION

A method and apparatus for configuring and displaying a user interface with healthcare studies. In one embodiment, the method comprises accessing user-specified configuration information for configuring a first user interface of a medical image management system, the first user interface to display a list of healthcare studies including one or more unread healthcare studies; creating the first user interface with the list of healthcare studies with priority information for the one or more unread healthcare studies, including determining the priority information, according to the user-specified configuration information, for at least one unread healthcare study in the list based on findings that result from performing automated image analysis on one or more of the images in said at least one unread healthcare study; and displaying the first user interface with the list of healthcare studies with the priority information on a display screen of medical image management system.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 5A illustrates one example of one embodiment of a user interface showing a list of healthcare studies.

FIG. 5B illustrates an example of different icons and sort orders that may appear in a priority color column of one embodiment of a list of healthcare studies.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Embodiments of the present invention are directed to systems, methods, and GUIs for rendering and displaying a list (e.g., a worklist) of healthcare studies with priority information (e.g., urgent, non-urgent, etc.) on a display device. In one embodiment, the display device is part of, or associated with, a medical image management system. In one embodiment, the system is configured to determine an order (e.g., sort) or priority for healthcare studies on the list using information from findings produced by automated image analysis algorithms applied to images in the healthcare studies. In one embodiment, the list is configurable for each image analysis algorithm (e.g., an artificial intelligence (AI) image analysis algorithm) and prioritized based on actual Machine Learning (ML) results, allowing the an individual, such as, for example, an individual of a hospital or other healthcare providing entity, to configure the system to present studies higher on a list based on an AI result severity. This enables the list of healthcare studies to present critical/emergent results at the top of the list, allowing for potentially quicker diagnosis. Having briefly described an overview of the present invention, embodiments of the invention will be discussed with reference to FIGS. 1-7.

The subject matter of embodiments of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Having briefly described embodiments of the present invention, an exemplary operating environment suitable for use in implementing embodiments of the present invention is described below.

Figure 1:
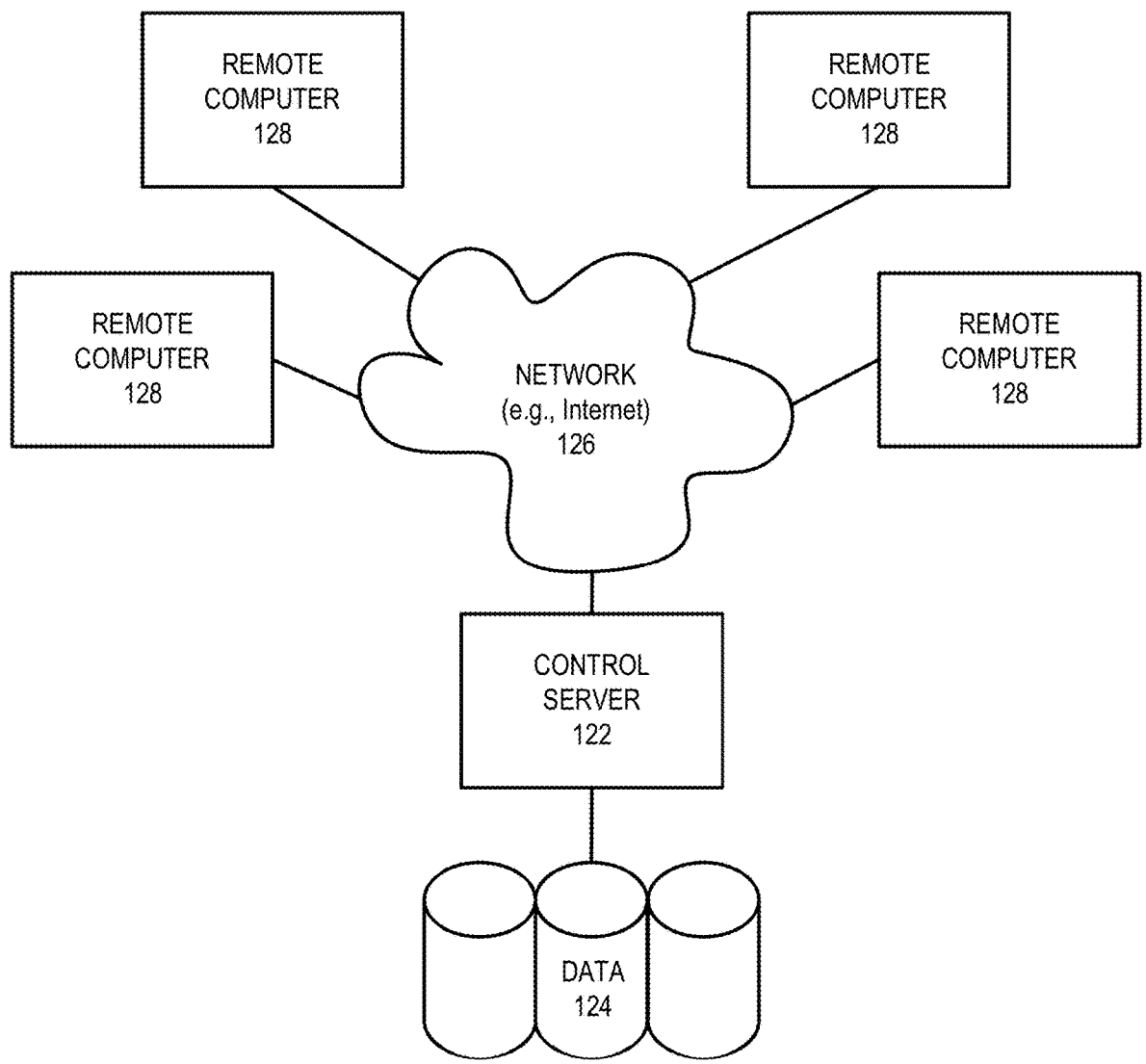
FIG. 1 illustrates an exemplary a medical information computing system environment, with which embodiments of the present invention may be implemented.

Referring to the drawings in general, and initially to FIG. 1 in particular, a medical information computing system environment, with which embodiments of the present invention may be implemented is illustrated and designated generally as reference numeral 120. It will be understood and appreciated by those of ordinary skill in the art that the illustrated medical information computing system environment 120 is merely an example of one suitable computing environment and is not intended to suggest any limitation as to the scope of use or functionality of the invention. Neither should the medical information computing system environment 120 be interpreted as having any dependency or requirement relating to any single component or combination of components illustrated therein.

Embodiments of the present invention may be operational with numerous general-purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 120 includes a general-purpose computing device in the form of a control server 122. Components of control server 122 may include, without limitation, a processing unit, internal system memory, and a suitable system bus for coupling various system components, including database cluster 124, with control server 122. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 122 typically includes therein, or has access to, a variety of computer-readable media, for instance, database cluster 124. Computer-readable media can be any available media that may be accessed by server 122, and includes volatile and nonvolatile media, as well as removable and non-removable media. By way of example, and not limitation, computer-readable media may include computer storage media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by control server 122. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 124, provide storage of computer-readable instructions, data structures, program modules, and other data for control server 122. Control server 122 may operate in a computer network 126 using logical connections to one or more remote computers 128. Remote computers 128 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as intensivists, surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, radiologic technologists, researchers, veterinarians, students, and the like. Remote computers 128 may also be physically located in non-traditional medical care environments so that the entire health care community may be capable of integration on the network. Remote computers 128 may be personal computers, servers, routers, network PCs, peer devices, other common network nodes, or the like, and may include some or all of the elements described above in relation to control server 122. The devices can be personal digital assistants or other like devices.

Exemplary computer networks 126 may include, without limitation, local area networks (LANs) and/or wide area networks (WANs). Such networking environments are commonplace in offices, enterprise-wide computer networks, intranets, and the Internet. When utilized in a WAN networking environment, the control server 122 may include a modem or other means for establishing communications over the WAN, such as the Internet. In a networked environment, program modules or portions thereof may be stored in association with control server 122, the database cluster 124, or any of remote computers 128. For example, and not by way of limitation, various application programs may reside on the memory associated with any one or more of remote computers 128. It will be appreciated by those of ordinary skill in the art that the network connections shown are exemplary and other means of establishing a communications link between the computers (e.g., control server 122 and remote computers 128) may be utilized.

In operation, a clinician may enter commands and information into control server 122 or convey the commands and information to control server 122 via one or more of remote computers 128 through input devices, such as a keyboard, a pointing device (commonly referred to as a mouse), a trackball, or a touch pad. Other input devices may include, without limitation, microphones, scanners, or the like. Commands and information may also be sent directly from a remote healthcare device to the control server 122. In addition to a monitor, control server 122 and/or remote computers 128 may include other peripheral output devices, such as speakers and a printer.

Although many other internal components of control server 122 and remote computers 128 are not shown, those of ordinary skill in the art will appreciate that such components and their interconnection are well known. Accordingly, additional details concerning the internal construction of control server 122 and remote computers 128 are not further disclosed herein.

Figure 2:
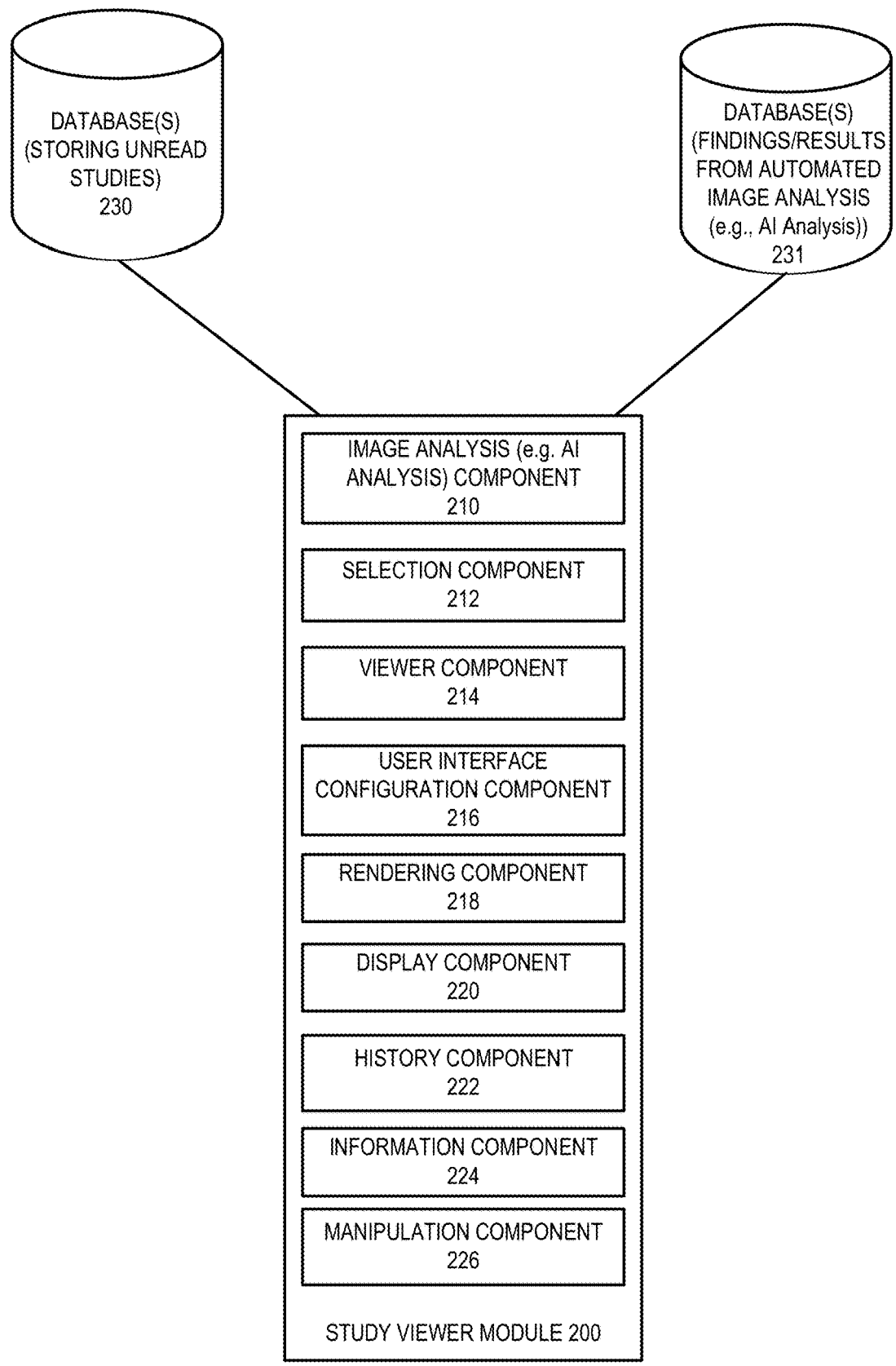
FIG. 2 is a block diagram showing one embodiment of a computing system architecture for displaying study healthcare study information (e.g., images, graphs, parameter values, etc.) in a graphical user interface (GUI).

With reference to FIG. 2, a block diagram is illustrated that shows an exemplary computing system architecture for simultaneous viewing of current and prior values of parameters from healthcare studies on a display screen. It will be appreciated that the computing system architecture shown in FIG. 2 is merely an example of one suitable computing system and is not intended as having any dependency or requirement related to any single module/component or combination of modules/components.

In one embodiment, the computing system includes a study viewer 200, one or more databases 230 storing and maintaining unread healthcare studies (and potentially other healthcare studies), and one or more databases 231 storing and maintaining findings that result from applying one or more automated image analysis algorithms (e.g., artificial intelligence (AI) analysis algorithms) to images of the unread healthcare studies such as those, for example, stored in databases 230. In one embodiment, the healthcare studies include images and study data, such as, for example, values of one or more medical parameters (e.g., measurements, etc.) related to the healthcare study. Exemplary medical images include radiology images, laboratory images, pictures, cardiology images, such as echocardiography images, and other healthcare images. One of skill in the art will appreciate that the databases may be maintained separately or may be integrated. Databases 230 may contain images or other study data (e.g., parameter values (e.g., measurements)) that are linked to a patient's electronic medical record (EMR), such that images and/or study data may be selected from within the EMR and displayed within a viewer via viewer component 214 or linked to a VNA (Vendor Neutral Archive) which stores, images, EKG's pictures, notes, etc. As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way. In one embodiment, the automated image analysis algorithms are AI analysis algorithms performed on the one or more images of healthcare studies. These algorithms may be applied remotely using one or more servers that receive the studies and their associated images and automatically apply the algorithms to those images. Alternatively, the AI analysis algorithms are applied locally on the images of the healthcare studies by image analysis component 210 after the studies have been received by the medical image management system. Alternatively, some of the algorithms are performed remotely while others are performed locally.

The algorithms produce findings that specified the results of the application of the algorithms on the images. In one embodiment, these algorithms produce textual findings that indicate possible conditions of a patient identified by the algorithm as well as an abnormality score with a magnitude that indicates a chance the patient has an abnormality based on the analysis performed on the images (e.g., the higher the score, the higher the chance). Note that in alternative embodiments, other scores, such as confidence levels of diagnosis, may be included in the findings from the algorithms.

In one embodiment, the medical image management system allows a user (e.g., a system administrator at a hospital or other medical facility), at a system level through their user-specified information, to control the priority displayed for healthcare studies in a worklist of studies presented to another user (e.g., physician, clinician, etc.) based on automated image analysis findings (e.g., AI analysis findings). That is, user-specified information prioritizes and/or configures a graphical user interface (GUI) (e.g., a user-sortable GUI) presenting the worklist of healthcare studies based on findings produced as part of automated image analysis results (e.g., AI analysis algorithms). In one embodiment, these findings may be textual findings, such as, for example, but not limited to, the words included in the findings produced by an image analysis algorithm on the images of the healthcare study. In one embodiment, the findings include a score (e.g., abnormality score, numerical confidence level indication associated with analysis results, etc.) prepared by the automated image analysis algorithm.

In one embodiment, the worklist of healthcare studies includes one or more unread healthcare studies, and each study of these healthcare studies is assigned a priority level by physician as part of the ordering process when the study is to be performed. Typically, the unread studies would be listed in the worklist according to this priority level assigned by the physician. However, by configuring the system, the user interface displaying the worklist is reconfigured to modify the priority of the healthcare study and/or the order in which the unread healthcare studies are listed based on findings that result from performing automated image analysis on one or more healthcare images of one or more studies in the worklist. In other words, the worklist could essentially be resorted by taking into account the findings from the automated image analysis. In one embodiment, a user is only able to configure the user interface to make the priority level (e.g., a priority level associated with results of applying AI image analysis) associated with an unread healthcare study higher than the physician's original priority. In other words, a user cannot configure the user interface to make a physician's priority at the time of ordering lower.

In one embodiment, the worklist is configured using a configuration graphical user interface (GUI) displayed by the medical image management system. In one embodiment, the GUI is a dialog box in which the user interacts using cursor control device using other well-known computer input devices of the medical image management system. In one embodiment, using the GUI, a user selects an urgency level and color to be displayed on the worklist with the healthcare study based on a score (e.g., abnormality score) supplied by image analysis algorithm and/or based on one or more keywords in the findings generated by the automated image analysis algorithm. Thus, a user configures the information that is displayed at the site (e.g., a color indicator used on a display screen) in a worklist of healthcare studies based from textual findings provided by an automated image analysis algorithm.

In one embodiment, the worklist is configured such that if a rule is created based on a textual finding in the results of an automated image analysis algorithm, then the score value from an image analysis algorithm is ignored for the purposes of adjusting the priority level of the healthcare study in the work list. That is, in one embodiment, when configuring the priority for the worklist, if the user selects priority levels based on both the abnormality score and one or more textual terms that appear in the findings, the priority level that is to be used and displayed for the healthcare study is the one associated with the textual findings.

Thus, using the techniques disclosed herein, based on user selections in a configuration user interface, the system configures a user interface for listing unread healthcare studies (and potentially previously reviewed studies) to display certain priority levels (e.g., emergent/urgent; critical, etc.) for each of the unread studies, when the priority levels are determined based on one or more key words and/or a score in the findings from the automated image analysis algorithm (e.g., AI analysis algorithm, etc.).

In one embodiment, the system automatically sorts the unread healthcare studies in the worklist based on their priority. In one embodiment, the sorting could occur in response to a user input or selection (e.g., selection of a column header) or automatically by the system. In one embodiment, the worklist allows up to three different sorts based on priority: (1) based on the doctor-specified priority, based on results based on an AI (or other automated image analysis) findings, or based on other patient or medical information (e.g., MRN, patient name, location, modality, etc.). In another embodiment, the worklist is sortable based on the doctor-specified priority when ordering the study, priority based on an AI (or other automated image analysis) textual findings, or priority based on an AI score (e.g., abnormality score).

Study viewer 200 receives and displays lists of healthcare studies along with images and other information from healthcare studies along with priority information. These healthcare studies may come from more than one source (e.g., database). Thus, a single storage repository or a single PACS system is not required. Study viewer 200 may reside on one or more computing devices, such as, for example, control server 122 described above with reference to FIG. 1. By way of example, control server 122 includes a computer processor and may be a server, personal computer, desktop computer, laptop computer, handheld device, mobile device, consumer electronic device, or the like.

Study viewer 200 comprises selection component 212, viewer component 214, user interface configuration component 216, rendering component 218, and display component 220. In various embodiments, study viewer module 200 includes a history component 222, an information component 224, and a manipulation component 226. It will be appreciated that while study viewer 210 is depicted as receiving healthcare studies stored in databases 230, study viewer module 200 may receive healthcare studies from multiple sources including databases spread across multiple facilities and/or multiple locations as well as findings that result from applying one or more automated image analysis algorithms (e.g., AI analysis algorithms) to images of the healthcare studies. It will also be appreciated that study viewer 200 may receive healthcare studies with their images and/or findings that result from the automated image analysis algorithms (e.g., AI analysis algorithms) from the sources described above via links within a patient's EMR.

Selection component 212 receives a selection of a healthcare study and causes a study to be opened. In one embodiment, the healthcare study comprises one or more series of images and one or more parameter values (e.g., measurements, findings, impressions, patient demographics and history/risk factors, etc.). In one embodiment, each series comprises one or more images depicting the subject of the image from various angles. A list perspective within a multimedia manager provides a list of available studies (including unread studies), images, and other media. A clinician can select the desired items to launch in the viewer. In one embodiment, the selection of desired items may be made within the EMR or VNA.

The healthcare study selected by selection component 212 may be listed as part of a list (e.g., worklist) of healthcare studies that includes priority information that indicates a priority level associated with each study. The list of healthcare studies may include only unread (e.g., un-reviewed) healthcare studies or both read and unread healthcare studies. The studies include priority information that indicates their priority level. In one embodiment, the priority information is specified for each healthcare study on the list. Alternatively, the priority information is only displayed for a subset of healthcare studies on the list (e.g., only unread healthcare studies have listed priority). The priority information may indicate that the study has a high priority (e.g., urgent or an emergency), a low priority (e.g., non-urgent), or another priority level in between. In one embodiment, the priority level of a study may be set by a physician or may be based on the findings from the automated image analysis algorithms (e.g., AI analysis algorithms). Note that priority information associated with both such priority levels may be displayed on the same interface. In either case, this allows a physician to quickly determine the priority associated with each unread healthcare study to help the physician decide on an order in which to review the studies.

User interface configuration component 216 configures one or more user interfaces presented by the medical image management system. In one embodiment, user interface configuration component 216 configures the list of studies from which a healthcare study may be selected by selection component 212 and controls, based on configuration information, the priority information that is presented with the list of studies. In one embodiment, user interface configuration component 216 receives user-specified configuration information that indicates whether the priority information to be displayed for each of the studies (e.g., unread studies) on the list is based on one or more of the information from findings from automated image analysis algorithms applied to images of the listed unread healthcare studies, physician-based prioritization and some other prioritization (e.g., based on other patient or modality information, based on a change in findings from a previous examination (e.g., a delta or a increased rate of change in the findings, etc.). In one embodiment, user interface configuration component 216 obtains this information from a user through a configuration user interface presented to the user under control of user interface configuration component 216.

Rendering component 218 accesses worklist configuration information created and stored in response to a user using the configuration user interface and generates a graphical user interface (GUI) that depicts a list of unread healthcare studies with priority information that is determined, as specified in the user-specified configuration information, based on one or more of the information from findings from automated image analysis algorithms applied to images of the one or more unread healthcare studies, physician-based prioritization and some other prioritization.

Display component 220 includes a graphical display device that may be a monitor, computer screen, project device or other hardware device for displaying graphical user interfaces containing images and other data from healthcare studies as well as findings that result from applying automated image analysis algorithms to images in the healthcare studies. Display component 220 displays the GUI generated by the rendering component 218 with the list of unread healthcare studies and the priority information. In one embodiment, the list of unread healthcare studies is sorted based on priority. In another embodiment, the list of unread healthcare studies is not sorted but the priority information clearly shown so that a physician is able to discern priority levels from the state of the display of unread healthcare studies (e.g., have higher priority and/or lower priority).

In one embodiment, a history component 222 displays a history of different studies and clinical images associated with more than one healthcare image. History component 222 further allows a selection of one or more images from the history to be displayed in the viewer by display component 220. For example, the selection component 212 may have received a selection from the clinician of a particular study. However, once display component 220 has displayed the images that comprise that selected study, history component 222 may display other studies and clinical images that are of particular interest to the clinician. The clinician may then select additional items from the history to launch within the viewer.

In one embodiment, information component 224 displays additional information associated with more than one healthcare image, the history, or a combination thereof. The additional information comprises patient identifying information, image related information, study related information, or a combination thereof. Such additional information may also include time related information.

In one embodiment, a manipulation component 226 allows a clinician to manipulate a display of a healthcare image. For example, a clinician may determine that the image as it is rendered within the viewer is not large enough to see a desired level of detail. The clinician may zoom in or out and manipulation component 226 manipulates the display of the image accordingly. Similarly, the clinician may desire to pan an image and the manipulation component 226 manipulates the image display accordingly.

Figure 3:
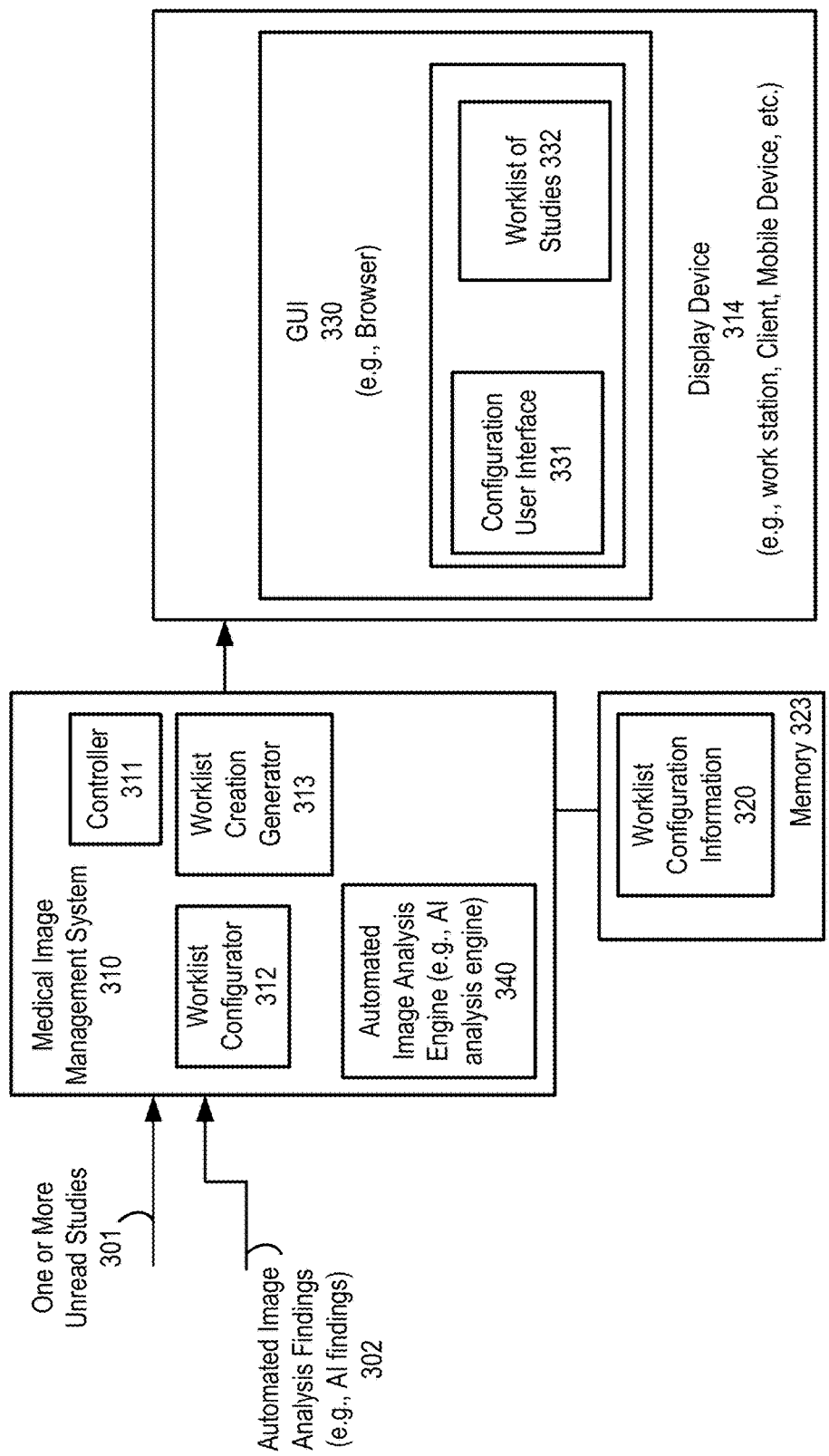
FIG. 3 is a data flow diagram of one embodiment of a process for configuring and displaying a list (e.g., a worklist) of unread healthcare studies with priority information based on findings from automated image analysis algorithms that have been applied to one or more of the images of the healthcare studies.

FIG. 3 is a data flow diagram of one embodiment of a process for configuring and displaying a list (e.g., a worklist) of unread healthcare studies with priority information determined based on findings from automated image analysis algorithms (e.g., AI analysis algorithm, etc.) that have been applied to one or more of the images of the healthcare studies. In one embodiment, the list is part of a worklist produced by a medical image management system.

Referring to FIG. 3, medical image management system 310 allows a user to configure a graphical user interface 330 used to display a list of unread healthcare studies to present priority information. The configuration controls how the priority for each study on the list is determined.

In one embodiment, the techniques disclosed herein allows users (e.g., a system administrator in a hospital or other medical facility) to configure how priority is determined for studies when applying automated image analysis algorithms to images of healthcare studies that are presented in a list (e.g., a worklist). In one embodiment, the automated image analysis algorithms comprise AI automated image analysis algorithms. In one embodiment, the users that can configure the user interface that displays the list of unread healthcare studies are limited to those with configuration privilege to configure the user interface of a medical image management system.

In one embodiment, the findings from applying automated image analysis algorithms to images of healthcare studies include an abnormality score. In an alternative embodiment, the medical image management system runs one or more of the automated image analysis algorithms. In one embodiment, the abnormality score is sent to the medical image management system. In one embodiment, the higher the number of the abnormality score, the greater chance of an abnormality was identified on one or more images in a study by the algorithm.

In on embodiment, in response to the abnormality score, the medical image management system allows a user to select the priority level to be displayed in a column of the list of healthcare studies. In one embodiment, the user (e.g., a system administrator in a hospital or other medical facility) selects the urgency and color display they would like to see in the column to indicate the priority level. In one embodiment, the selected urgency and color display are used when the abnormality score is at a user-selected level or higher for the individual algorithm.

In one embodiment, the priority level and its associated color display are derived from textual findings sent by the automated image analysis algorithm (e.g., AI algorithm). In this case, the system allows a user to identify one or more keywords and if such words are contained (or not contained) in the findings, the colors selected during configuration are displayed in a column of the worklist (e.g., the icon worklist column). For example, a user could specify that if a keyword such as, for example, "pneumothorax", is part of the finding, a predetermined priority level is displayed for the healthcare study that had that automated image analysis algorithm applied to it.

In one embodiment, the priority level is configured for each automated image analysis engine (e.g., AI image analysis engine) that is used to perform image analysis on images of the healthcare studies. In one embodiment, these engines may be integrated into the medical image management system, such as shown with automated image analysis engine (e.g., AI analysis engine, etc.) 340. In another embodiment, one or more of these engines are located remotely with respect to the medical image management system. In such a case, the results (findings) from using these engines to apply the automated image analysis algorithm(s) to the images are sent, via wired or wireless communications, to the medical image management system.

Controller 311 controls operations of medical image management system 310. In one embodiment, controller 311 comprises one or more processors, microcontrollers, and/or a combination of hardware, software and/or firmware. In one embodiment, controller 311 responds to user-specified configuration information to cause medical image management system 310 to generate a list of unread studies prioritized according to a user-specified prioritization. The user-specified configuration information determines whether the user-specified prioritization takes into account one or more of the information from findings from automated image analysis algorithms applied to images of the one or more unread healthcare studies, physician-based prioritization and some other prioritization.

One or more unread healthcare studies 301 are received by a medical image management system 310 along with findings or results 302 from one or more automated image analysis algorithms applied to images of the one or more unread healthcare studies 301. In one embodiment, one or more unread healthcare studies 301 are sent from one or more medical imaging modalities that perform medical imaging (e.g., cardiovascular (CV), X-ray radiography, magnetic resonance imaging, ultrasound, endoscopy, tactile imaging, thermography, nuclear medicine functional imaging techniques such as positron emission tomography (PET) and single-photon emission computed tomography (SPECT), etc.). In another embodiment, one or more unread healthcare studies 301 are received by medical image management system 310 from a remote location. In one embodiment, the remote location may comprises one or more modalities that create the studies or a remotely located image repository (e.g., a picture archiving and communication system (PACS), VNA, etc.).

After the unread healthcare studies 301 and the automated image analysis findings (e.g., findings 302) are obtained, worklist creation layout generator 313 obtains the worklist configuration information 320 from memory 323 and uses that information to display a worklist of studies 332 in a GUI (or viewer) 330 on display device 314. This allows a physician or other medical profession to easily see the studies that have been received and the priority at which they need to be reviewed. An example of such a worklist is shown in FIGS. 5A-B and is described in more detail below.

Worklist configuration information 320 is generated by a worklist configurator 312, which under direction of controller 311, causes a configuration user interface 331 to displayed in a GUI (or viewer) 330 on display device 314. A user is able to interact with configuration user interface 331 to configure the unread studies worklist with priority information that is determined by taking into account one or more of the information from findings from automated image analysis algorithms applied to images of the one or more unread healthcare studies, physician-based prioritization and some other prioritization. An example of one embodiment of a configuration user interface is shown in FIG. 4 and described in more detail below.

After the user specifies how the priority information for the unread studies is shown in the worklist is to be determined, the worklist configuration information containing the information for configuring the user interface listing of healthcare studies is stored in memory 323 for access when new studies are received by medical image management system 310 and the list of unread healthcare studies is to be displayed.

Figure 4:
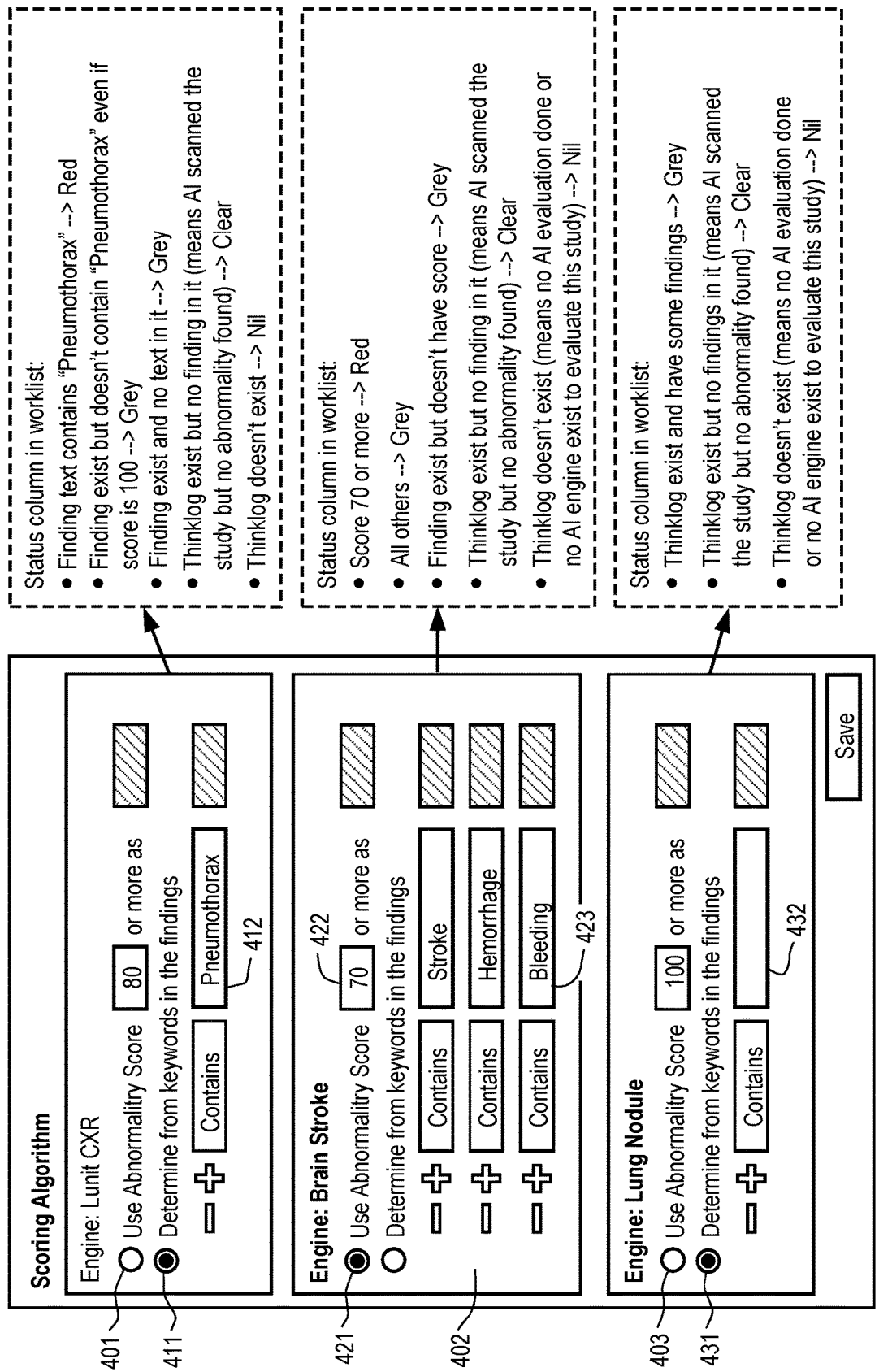
FIG. 4 illustrates an example of a user interface that may be used to configure the worklist GUI displayed that lists unread studies and their associated priority levels.

FIG. 4 illustrates an example of a user interface that may be used to configure the worklist GUI displayed that lists unread studies and their associated priority levels. Referring to FIG. 4, the GUI displays three windows 401-403, one for each engine that may provide results or findings from application of an automated image analysis algorithm to one or more images of a healthcare study. Although only three windows are shown, one skilled in the art would recognize that the GUI may have more than or less than three such windows and can have a window for each automated image analysis engine from which the medical image management system could expect to receive results.

In window 401, a user has selected to configure the priority of any healthcare studies on the worklist GUI that have results from a C×R image analysis engine that runs an image analysis algorithm. In this case, the user selects circle 411 and inserts the word "Pneumothorax" in window 412 to specify a condition that the finding has the word "Pneumothorax". In this case, the status column in the worklist indicating the priority would have:

1) a color red if the text in the findings contains the work "Pneumothorax", 2) a color grey if there are findings but the text in the findings does not contain the work "Pneumothorax", 3) a color grey if there are findings but there is no text in the findings, 4) a clear circle if the automated image analysis was performed and there are no findings in it (indicating that automated image analysis algorithm but no abnormality was found (e.g., its clear), or 5) nil, which indicates that the automated image analysis was not performed.

In window 402, a user has selected to configure the priority of any healthcare studies on the worklist GUI that have results from a Brain Stroke image analysis engine that runs an image analysis algorithm. In this case, the user selects circle 421 and inserts an abnormality score of "70" in window 422 to specify a condition that the finding has an abnormality score of at least 70. Because circle 421 was selected, the words entered into windows 423 are ignored. In this case, the status column in the worklist indicating the priority would have:

1) a color red if the abnormality score from the Brain Stroke engine is 70 or greater, 2) a color grey in all other cases, 3) a color grey if there are findings but there is no abnormality score, 4) a clear circle—the automated image analysis was performed and there are no findings in it (indicating that automated image analysis algorithm but no abnormality was found (e.g., its clear)

5) nil, which indicates that the automated image analysis was not performed.

In one embodiment, in window 403, a user has selected to configure the priority of any healthcare studies on the worklist GUI that have results from a Lung Nodule image analysis engine that runs an image analysis algorithm. In this case, the user selects circle 431 but doesn't insert any keyword into window 432 to specify a condition that the finding has a particular keyword. In this case, the status column in the worklist indicating the priority would have:

1) a color grey if there are findings, 2) a clear circle if the automated image analysis was performed and there are no findings in it (indicating that automated image analysis algorithm but no abnormality was found (e.g., its clear), 3) nil, which indicates that the automated image analysis was not performed.

In one embodiment, while the priority level that is displayed can be changed based on the score from the image analysis algorithm, the score (e.g., an abnormality score, etc.) is it existed when received from engine. In other words, the score from the algorithm is not changed. In alternative embodiments, the abnormality score may be changed. Such a change may be due to information that is not from the image analysis algorithm or may be from another image analysis algorithm (e.g., an averaging or other numerical function is applied to the scores).

In one embodiment, the priority level status can only be set to make it indicate urgent (e.g., red for a color display) and a default color (e.g., grey), the latter being used when no rule is configured or when a configuration rule not applicable. Note that other colors may be used to convey priority.

In one embodiment, when a text-based rule is applied (e.g., a textual finding triggers a change in the priority level), the score value that is in the findings is ignored when deciding the priority level status, even if score is at a maximum level (e.g., 100).

In one embodiment, the text-based rule is only triggered with the "contains" option when a user selects the plus sign (see FIG. 4). In another embodiment, the text-based rule can operate to modify priority if a finding does not contain a particular word or words. In one embodiment, this occurs when a user selects the minus sign (see FIG. 4).

FIG. 5A illustrates one example of a user interface showing a list of healthcare studies. Referring to FIG. 5A, a GUI with a worklist of healthcare studies has a priority level column 500, a priority color column 501, and a score column 502. Priority level column 500 provides information that indicates the priority level set by the physician when ordering the examination (e.g., Routine, STAT, Urgent, Pre-Op, etc.). Priority color column 501 is the priority set by the image analysis findings (e.g., the AI analysis findings). In one embodiment, this column shows the color as determined by the user-specified configuration information based on the user-specified priority configuration information (e.g., based on finding from image analysis algorithms, physician-specified priority, etc.), while score column 502 contains the abnormality score (or other confidence level score or algorithm score) from the image analysis algorithm.

FIG. 5B illustrates an example of different icons and sort orders that may appear in the priority color column (e.g., the icon column). Depending on the algorithm vendor, and if additional information is provided, additional configuration values may be added as additional criteria to further refine the sorting.

In one embodiment, the information in the GUI worklist scoring column can be sorted ascending or descending and also sorted with other columns. Note that the reason a user would want to sort on various factors is that the image analysis algorithm (e.g., AI analysis algorithm, etc.) may find something on an image and assign a high abnormality score, but that doesn't mean it requires immediate attention from a user to diagnose.

Thus, using the techniques described above, the medical image management system configures the user interface of the list of healthcare studies to allow priority associated with healthcare studies in the list of healthcare studies to be configured based on findings the automated image analysis algorithms may have textual findings or an abnormality score that warrants a higher probability than originally assigned by a physician ordering the examination.

Figure 6:
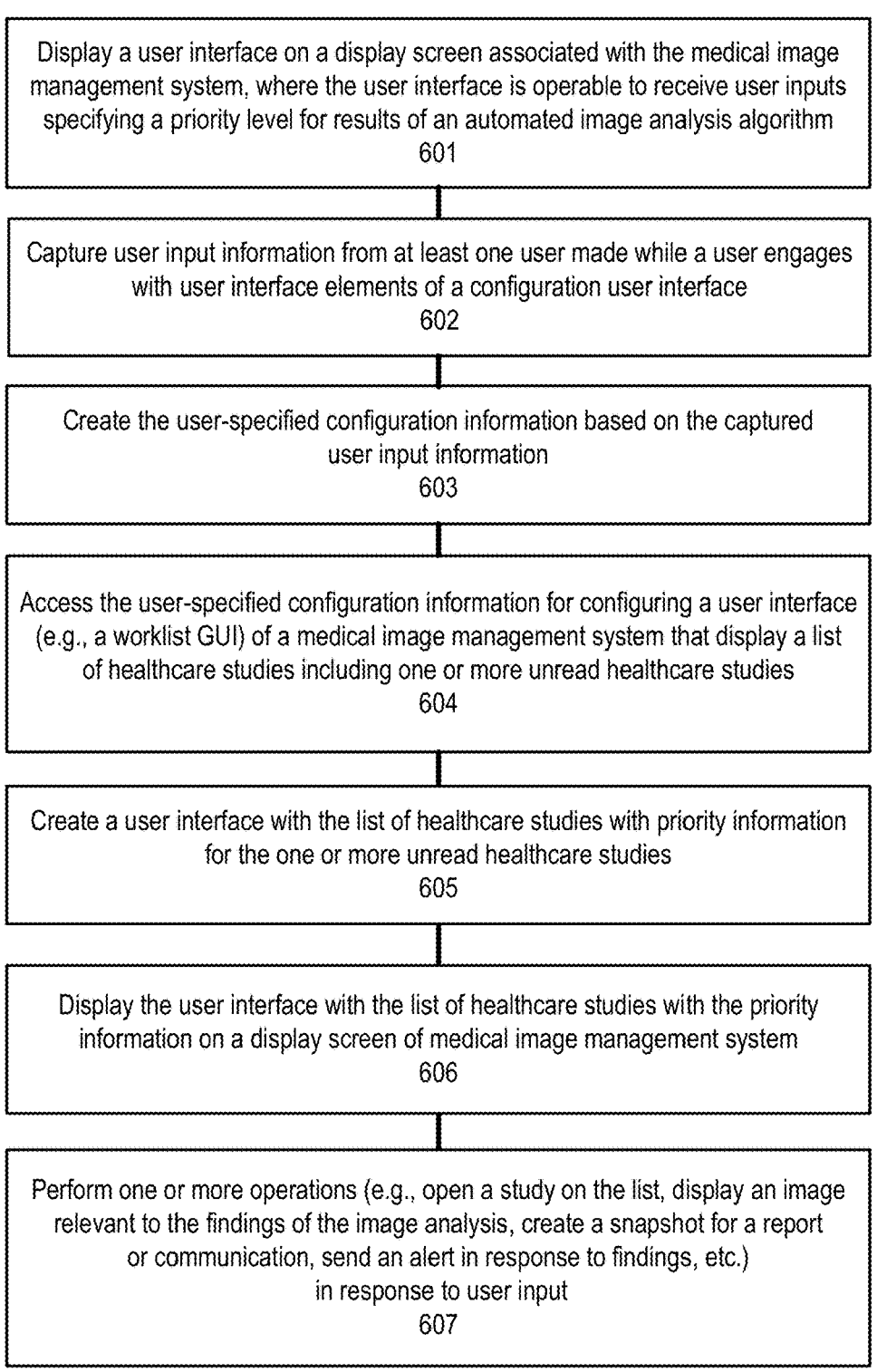
FIG. 6 is a flow diagram of one embodiment of a process for configuring and generating a list of healthcare studies with priority information.

FIG. 6 is a flow diagram of one embodiment of a process for configuring and generating a list of healthcare studies with priority information. In one embodiment, the processes are performed by processing logic that may comprise hardware (circuitry, dedicated logic, etc.), software (e.g., software running on a chip), firmware, or a combination of the three. In one embodiment, the process is performed by a medical image management system.

Referring to FIG. 6, the process begins by processing logic displaying a user interface on a display screen associated with the medical image management system, where the user interface is operable to receive user inputs specifying a priority level for results of an automated image analysis algorithm (processing block 601). In one embodiment, this user interface receives user input to set a priority level according to findings of automated image analysis algorithms on a per automated image analysis algorithm basis. In one embodiment, the user interface is responsive to user inputs to set priority of a healthcare study based on one or both of a numerical value and textual findings resulting from applying an image analysis algorithm to one or more images in the healthcare study. In one embodiment, the numerical value comprises an abnormality score. In one embodiment, the user interface allows a user to specify a range for the numerical value associated with a priority level.

In one embodiment, the priority information indicates whether automated image analysis was performed on at least one image in each healthcare study and, if image analysis was performed, one or more of: findings exist and contain one or more keywords specified via the user interface; findings exist but do not contain one or more keywords specified via the user interface; findings exist but no text is contained in the findings; and no findings exist.

Using the user interface, processing logic captures user input information from at least one user made while a user engages with user interface elements of a configuration user interface (processing block 602) and create the user-specified configuration information based on the captured user input information (processing block 603). In one embodiment, the user-specified configuration information specifies how the priority information is determined and depicted in a worklist GUI listing unread healthcare studies. In one embodiment, user-specified configuration information is stored in a memory for later access to configure a user interface that lists healthcare studies and associated priority levels when new healthcare studies are received for review.

Subsequently, when a list of unread healthcare studies is to be displayed in a user interface, processing logic accesses the user-specified configuration information for configuring a user interface (e.g., a worklist GUI) of a medical image management system that display a list of healthcare studies including one or more unread healthcare studies (processing block 604). In one embodiment, accessing the user-specified configuration information occurs in response to the medical image management system receiving an indication that one or more unread healthcare studies have been generated.

Using the user-specified configuration information, processing logic creates a user interface with the list of healthcare studies with priority information for the one or more unread healthcare studies (processing block 605). In one embodiment creating the user interface includes determining the priority information, according to the user-specified configuration information, for at least one unread healthcare study in the list based on findings that result from performing automated image analysis on one or more of the images in the unread studies.

Processing logic displays the user interface with the list of healthcare studies with the priority information on a display screen of medical image management system (processing block 606).

Once the list of healthcare studies has been generated, processing logic performs one or more operations (e.g., open a study on the list, display an image relevant to the findings of the image analysis, create a snapshot for a report or communication, send an alert in response to findings, etc.) in response to user input (processing block 607). In one embodiment, the operations include receiving a user input indicating selection of a healthcare study on the list, and in response to receiving the user input, opening the healthcare study and displaying one or more images from the healthcare study. In another embodiment, the operations including receiving a user input (e.g., a cursor click or other indication) in user interface and having the study open to an image that shows or correlates to the finding. In yet another embodiment, the operations include creating a snapshot of an image in one of the unread healthcare studies, where the image depicts information associated with a finding that resulted applying an automated image analysis algorithm to the image, and exporting the snapshot into a medical report, chat or other form of communication.

In one embodiment, the user-specified configuration information indicates that an alert (e.g., SMS, text, email, or other message, a chat indication indicating a chat session is desired with the physician, etc.) is to be sent in response to a predetermined finding in the results of automated image analysis performed one or more image of a healthcare study. In one embodiment, the alert is sent to one or more predetermined healthcare providers responsible for handling a condition associated with the predetermined finding. In one embodiment, the alert includes a link to an image related to the findings of the health care study that were generated by the automated image analysis algorithm. In such a case, the alert may include a link that the user selects to open a study containing the image associated with finding and the system displays the image. Note that the sending of the alert can occur automatically in response to the findings and is not dependent nor need wait until the list of healthcare studies is displayed.

Other operations may be performed as well.

An Exemplary Medical Imaging Management System

Figure 7:
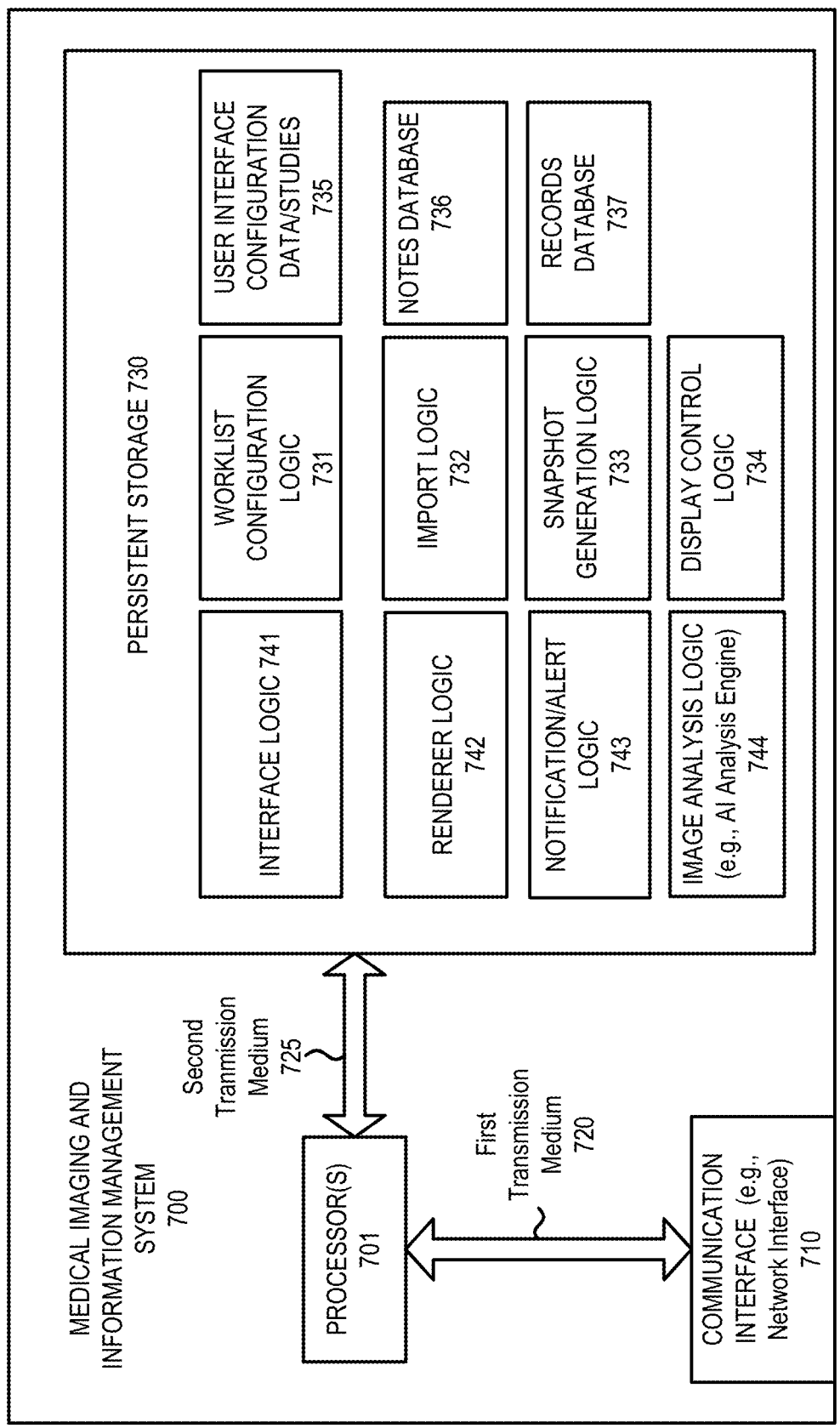
FIG. 7 illustrates an exemplary embodiment of a logical representation of a medical imaging and information management system that generates and renders images from healthcare studies.

FIG. 7 illustrates an exemplary embodiment of a logical representation of a medical imaging and information management system 700 that generates and renders layouts with current and prior values of parameters discussed above. In one embodiment, system 700 is part of a medical image system such as detailed above.

The medical imaging and information management system 700 includes one or more processors 701 that are coupled to communication interface logic 710 via a first transmission medium 720. The communication interface logic 710 enables communications with other electronic devices, specifically enabling communication with remote users such as doctors, nurses and/or medical technicians, remote databases (e.g., PACS) that store healthcare studies, healthcare modalities that generate and send studies and one or more remote locations (e.g., cloud-based servers) that apply image analysis algorithms to images of studies and generate findings based on the results. According to one embodiment of the disclosure, communication interface logic 710 may be implemented as a physical interface including one or more ports for wired connectors. Additionally, or in the alternative, communication interface logic 710 may be implemented with one or more radio units for supporting wireless communications with other electronic devices.

Processor(s) 701 is further coupled to persistent storage 730 via $2^{nd}$ transmission medium 725. According to one embodiment of the disclosure, persistent storage 730 may include (a) user interface logic 741, (b) rendering logic 742, (c) notification/alert logic 743, (d) worklist configuration logic 731, (e) an import logic 732, (f) a snapshot generation logic 733, (g) a display control logic 734, (h) user interface configuration database 735, (i) a notes database 736 and (j) a records database 737.

Worklist configuration logic 731 includes logic for generating a worklist configuration GUI to enable a user to set how the system determines priority that is displayed with healthcare studies on a list of healthcare studies. In one embodiment, logic 731 performs the operations associated and described in conjunction with the user interface of FIG. 4 including displaying the user interface and capturing the user's interactions with the user interface to create user-specified configuration information that is accessed in the future to direct priority information determination and generation for a user interface listing healthcare studies for review. In one embodiment, the priority information is determined based on findings that results from apply automated image analysis algorithms (e.g., AI analysis algorithms, etc.) to images of the healthcare studies.

In one embodiment, user interface logic 741 includes logic for enabling interaction between a user and the display areas being displayed on the display screen. The user interfaces include both the configuration user interface that enables a user to set how the priority in a list of healthcare studies (e.g., a GUI worklist) is determined and the user interface that lists the healthcare studies (e.g., unread healthcare studies) with the priority information as determined based on the user-specified configuration information captured from a user's interactions with the configuration user interface. The user interface configuration and study database 735 stores the user-specified configuration information along with healthcare studies and their associated images and data (e.g., results or findings).

Rendering logic 742 includes logic for generating data for user interfaces, such as those, for example, described above. In one embodiment, the rendering logic 742 performs one or more processing operations on data of healthcare studies to generate display data for displaying the content of the study, including any images and findings contained therein.

Notification/alert logic 743 includes logic to issue and send notifications and/or alerts for study reviews to one or more of physicians and medical personnel. In one embodiment, notification/alert logic 743 sends an alert (e.g., SMS, text, email, or other message, a chat indication indicating a chat session is desired with the physician, etc.) in response to a predetermined finding in the results of automated image analysis performed one or more image of a healthcare study. In one embodiment, the predetermined finding comprises an abnormality score above a threshold level. In another embodiment, the predetermined finding comprises one or more keywords in the findings. In yet another embodiment, the predetermined finding comprises an abnormality score above a threshold level and one or more keywords in the findings. In one embodiment, the alert is sent to one or more predetermined healthcare providers responsible for handling a condition associated with the predetermined finding. For example, in one embodiment, if the findings indicate the patient has likely experienced a brain stroke, an alert is automatically sent to a stroke team at a particular medical facility to take care of the patient. In one embodiment, the alert includes a link to an image related to the findings of the health care study that were generated by the automated image analysis algorithm. In such a case, the alert may include a link that the user selects to open a study containing the image associated with finding and the system displays the image.

Image analysis logic 744 performs one or more image analysis algorithms on images from healthcare studies. In one embodiment, the image analysis algorithms are AI analysis algorithms. The results from applying the image analysis algorithms are used to determine the priority levels displayed with the healthcare studies upon which the algorithms were applied.

Import logic 732 may include logic for retrieving one or more pieces of information from a storage device and importing each of the one or more pieces of information into a separate display area of a viewer or viewer template. For example, the pieces of information may include, but are not limited or restricted to, (i) findings from automated image analysis algorithms (e.g., AI algorithms); (ii) medical images, including x-rays, mammograms, computerized tomography (CT) scans, magnetic resonance imaging (MRI), positron emission tomography (PET) scan and/or ultrasound imaging, (iii) physician's notes regarding one or more of the medical images and/or (iv) medical records corresponding to one or more of the subjects of the one or more medical images.

Snapshot generation logic 733 includes logic for saving at least a first state of the layout template. Saving the first state may include storing, at least, (i) the one or more pieces of information, and (ii) viewing properties of each of the one or more pieces of information in a non-transitory computer-readable medium. The layout template may depict one or more images of a healthcare study that depicts image data that is relevant to a finding from an automated image analysis algorithm. Snapshot generation logic 733 is able to save the snapshot into a medical record or report and/or send the snapshot to a predetermined location.

Display control logic 734 includes logic for displaying user interfaces and images that have been rendered locally as discussed above. In one embodiment, display control logic 734 includes logic to display a browser into which the images, user interfaces described above, and lists (e.g., worklists) are displayed.

Images and parameter values database 735, the notes database 736 and records database 737 may comprise a single non-transitory computer-readable medium storage device or may each be a separate non-transitory computer-readable medium storage device. The images database 735 stores parameter values and medical images that a user may import into a display area of a viewer or other GUI. Notes database 736 stores notes recorded by a doctor, nurse, medical technician, etc., that a user may import into a display area of a layout template. Finally, records database 737 stores medical records that a user may import into a display area of a layout template.

There is a number of example embodiments described herein.

Example 1 is a method comprising: accessing user-specified configuration information for configuring a first user interface of a medical image management system, the first user interface to display a list of healthcare studies including one or more unread healthcare studies; creating the first user interface with the list of healthcare studies with priority information for the one or more unread healthcare studies, including determining the priority information, according to the user-specified configuration information, for at least one unread healthcare study in the list based on findings that result from performing automated image analysis on one or more of the images in said at least one unread healthcare study; and displaying the first user interface with the list of healthcare studies with the priority information on a display screen of medical image management system.

Example 2 is the method of example 1 that may optionally include that accessing the user-specified configuration information occurs in response to the medical image management system receiving an indication that one or more unread healthcare studies have been generated.

Example 3 is the method of example 1 that may optionally include receiving a user input indicating selection of a healthcare study on the list; and in response to receiving the user input, opening the healthcare study, and displaying one or more images from the healthcare study.

Example 4 is the method of example 1 that may optionally include displaying a second user interface on a display screen associated with the medical image management system, the second user interface to receive user inputs specifying a priority level for results of an automated image analysis algorithm; capturing user input information from at least one user input made while a user engages with user interface elements of the second user interface; and creating the user-specified configuration information based on the user input information.

Example 5 is the method of example 4 that may optionally include that the second user interface is operable to receive user input to set a priority level for findings of automated image analysis algorithms on a per automated image analysis algorithm basis.

Example 6 is the method of example 4 that may optionally include that the second user interface is responsive to user inputs to set priority of a healthcare study based on one or both of a numerical value and textual findings resulting from applying an image analysis algorithm to one or more images in the healthcare study.

Example 7 is the method of example 6 that may optionally include that the numerical value comprises an abnormality score.

Example 8 is the method of example 6 that may optionally include that the second user interface allows a user to specify a range for the numerical value associated with a priority level.

Example 9 is the method of example 1 that may optionally include that the priority information indicates whether automated image analysis was performed on at least one image in each healthcare study and, if image analysis was performed, one or more of findings exist and contain one or more keywords specified via the user interface, findings exist but do not contain one or more keywords specified via the user interface, findings exist but no text is contained in the findings, and no findings exist.

Example 10 is the method of example 1 that may optionally include that the user-specified configuration information indicates that an alert is to be sent in response to a predetermined finding in the results of automated image analysis performed one or more image of a healthcare study.

Example 11 is the method of example 10 that may optionally include that the alert comprises a message or chat indication.

Example 12 is the method of example 10 that may optionally include that the alert includes a link to an image, and further comprising: receiving a user selection of the link; opening a study containing an image associated with the link; and displaying the image.

Example 13 is the method of example 10 that may optionally include sending the alert to one or more predetermined healthcare providers responsible for handling a condition associated with the predetermined finding.

Example 14 is the method of example 1 that may optionally include creating a snapshot of an image in one of the unread healthcare studies, the image depicting information associated with a finding from applying an automated image analysis algorithm to the image; and exporting the snapshot into a medical report.

Example 15 is a system a network communication interface to receive healthcare studies; a memory coupled to the network communication interface to store received healthcare studies; a display screen coupled to the memory to display the received healthcare studies; and one or more processors coupled to the network connection interface, the memory and the display screen and configured to access the user-specified configuration information for configuring a first user interface of a medical image management system, the first user interface to display a list of healthcare studies including one or more unread healthcare studies, create the first user interface with the list of healthcare studies with priority information for the one or more unread healthcare studies, wherein the first user interface determining the priority information, according to the user-specified configuration information, for at least one unread healthcare study in the list based on findings that result from performing automated image analysis on one or more of the images in said at least one unread healthcare study, and display the first user interface with the list of healthcare studies with the priority information on the display screen.

Example 16 is the system of example 15 that may optionally include that at least one processor of the one or more processors is further operable to: display a second user interface on the display screen associated with the medical image management system, the second user interface to receive user inputs specifying a priority level for results of an automated image analysis algorithm; cause the capture of user input information from at least one user input made while a user engages with user interface elements of the second user interface; and create the user-specified configuration information based on the user input information.

Example 17 is the system of example 16 that may optionally include that the second user interface is operable to receive user input to set a priority level for findings of automated image analysis algorithms on a per automated image analysis algorithm basis.

Example 18 is the system of example 16 that may optionally include that the second user interface is responsive to user inputs to set priority of a healthcare study based on one or both of a numerical value and textual findings resulting from applying an image analysis algorithm to one or more images in the healthcare study.

Example 19 is the system of example 18 that may optionally include that the numerical value comprises an abnormality score.

Example 20 is the system of example 18 that may optionally include that the second user interface allows a user to specify a range for the numerical value associated with a priority level.

Example 21 is the system of example 15 that may optionally include that the priority information indicates whether automated image analysis was performed on at least one image in each healthcare study and, if image analysis was performed, one or more of findings exist and contain one or more keywords specified via the user interface, findings exist but do not contain one or more keywords specified via the user interface, findings exist but no text is contained in the findings, and no findings exist.

Example 22 is the system of example 15 that may optionally include that the user-specified configuration information indicates that an alert is to be sent in response to a predetermined finding in the results of automated image analysis performed one or more image of a healthcare study, and wherein at least one processor of the one or more processors is further operable to send, via the network communication interface, the alert to one or more predetermined healthcare providers responsible for handling a condition associated with the predetermined finding.

Example 23 is a non-transitory computer readable storage media having instructions stored thereupon which, when executed by a system having at least a processor, a memory and a display screen therein, cause the system to perform a method comprising: accessing user-specified configuration information for configuring a first user interface of a medical image management system, the first user interface to display a list of healthcare studies including one or more unread healthcare studies; creating the first user interface with the list of healthcare studies with priority information for the one or more unread healthcare studies, including determining the priority information, according to the user-specified configuration information, for at least one unread healthcare study in the list based on findings that result from performing automated image analysis on one or more of the images in said at least one unread healthcare study; and displaying the first user interface with the list of healthcare studies with the priority information on a display screen of medical image management system.

Example 24 is the computer readable storage media of example 23 that may optionally include that the method further comprises: displaying a second user interface on a display screen associated with the medical image management system, the second user interface to receive user inputs specifying a priority level for results of an automated image analysis algorithm; capturing user input information from at least one user input made while a user engages with user interface elements of the second user interface; and creating the user-specified configuration information based on the user input information.

Example 25 is the computer readable storage media of example 24 that may optionally include that the second user interface is operable to receive user input to set a priority level for findings of automated image analysis algorithms on a per automated image analysis algorithm basis.

Example 26 is the computer readable storage media of example 24 that may optionally include that the second user interface is responsive to user inputs to set priority of a healthcare study based on one or both of a numerical value and textual findings resulting from applying an image analysis algorithm to one or more images in the healthcare study.

Example 27 is the computer readable storage media of example 26 that may optionally include that the numerical value comprises an abnormality score.

Example 28 is the computer readable storage media of example 26 that may optionally include that the second user interface allows a user to specify a range for the numerical value associated with a priority level.

Example 29 is the computer readable storage media of example 23 that may optionally include that the priority information indicates whether automated image analysis was performed on at least one image in each healthcare study and, if image analysis was performed, one or more of findings exist and contain one or more keywords specified via the user interface, findings exist but do not contain one or more keywords specified via the user interface, findings exist but no text is contained in the findings, and no findings exist.

Example 30 is the computer readable storage media of example 23 that may optionally include that the user-specified configuration information indicates that an alert is to be sent in response to a predetermined finding in the results of automated image analysis performed one or more image of a healthcare study, and wherein the method further comprises sending the alert to one or more predetermined healthcare providers responsible for handling a condition associated with the predetermined finding.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. A method comprising:
   obtaining, by one or more processors, healthcare studies, wherein the healthcare studies comprise one or more unread healthcare study and one or more read healthcare study, wherein each read healthcare study was assigned a priority level by a medical user;
   accessing user-specified configuration information for configuring a first user interface of a medical management system, wherein the user-specified configuration information comprises one or more keywords, wherein the one or more keywords each comprise textual findings provided by an automated image analysis algorithm, wherein the image analysis algorithm previously automatically identified the textual findings in one or more images in one or more unread healthcare studies by performing an automated image analysis, the first user interface to display a list of the healthcare studies;
   determining priority information for the healthcare studies in the list, according to the user-specified configuration information, wherein the determining comprises:
      for each unread healthcare study of the one or more unread healthcare studies, assigning a priority level to one or more images of a series of images comprising the unread healthcare study, according to the user-specified configuration information, based on performing the automated image analysis on the series of images in the unread healthcare study, wherein the automated image analysis comprises utilizing an image analysis algorithm to perform a textual analysis to locate the one or more keywords in the one or more images of the series of images, wherein the user-specified configuration information comprises pre-defined priority levels for images comprising each keyword of the one or more keywords and not comprising any keyword of the one or more keywords; and
      for each read healthcare study of the one or more read healthcare studies, according to the user-specified configuration information, obtaining the priority level assigned by the medical user;
   creating the first user interface with the list of the healthcare studies with the priority information comprising the priority levels of the one or more read healthcare studies and the one or more unread healthcare studies, based on the determining;
   displaying the first user interface with the list of healthcare studies with the priority information on a display screen of the medical image management system; and
   sending, by the medical image management system, independent of the displaying the first user interface, an automated alert, responsive to one or more of the findings from the automated image analysis, wherein the user-specified configuration information indicates that the automated alert is to be sent in response to a predetermined finding in the results of automated image analysis performed on one or more image of a healthcare study, wherein the sending comprises sending the automated alert to one or more predetermined healthcare providers responsible for handling a condition associated with the predetermined finding, and wherein the automated alert comprises the one or more keywords.

2. The method defined in claim 1, wherein accessing the user-specified configuration information occurs in response to the medical image management system receiving an indication that the one or more unread healthcare studies have been generated.

3. The method defined in claim, 1 further comprising:
receiving a user input indicating selection of a healthcare study on the list; and
in response to receiving the user input,
opening the healthcare study, and
displaying one or more images from the healthcare study.

4. The method defined in claim 1, further comprising:
displaying a second user interface on a display screen associated with the medical image management system, the second user interface to receive user inputs specifying a priority level for results of an automated image analysis algorithm;
capturing user input information from at least one user input made while a user engages with user interface elements of the second user interface, wherein the second user interface is responsive to user inputs to set priority of a healthcare study based on one or both of a numerical value and the one or more keywords; and
creating the user-specified configuration information based on the user input information, wherein if the user sets the priority based on both the numerical value and the one or more keywords, a priority associated with the one or more keywords is displayed as the priority for the healthcare study.

5. The method defined in claim 4, wherein the second user interface is operable to receive user input to set a priority level for findings of automated image analysis algorithms on a per automated image analysis algorithm basis.

6. The method defined in claim 4, wherein the numerical value comprises an abnormality score.

7. The method defined in claim 4, wherein the second user interface allows a user to specify a range for the numerical value associated with a priority level.

8. The method defined in claim 1, wherein the priority information indicates whether automated image analysis was performed on at least one image in each healthcare study and, if image analysis was performed, one or more of
findings exist and contain one or more keywords specified via the user interface,
findings exist but do not contain one or more keywords specified via the user interface,
findings exist but no text is contained in the findings, and
no findings exist.

9. The method defined in claim 1, wherein the automated alert comprises a message or chat indication.

10. The method defined in claim 1, wherein the automated alert includes a link to an image, and further comprising:
receiving a user selection of the link;
opening a study containing an image associated with the link; and
displaying the image.

11. The method defined in claim 1, further comprising:
creating a snapshot of an image in one of the one or more unread healthcare studies, the image depicting information associated with a finding from applying an automated image analysis algorithm to the image; and
exporting the snapshot into a medical report.

12. The method of claim 1, wherein the text comprising each of the one or more keywords consists of a word consisting of letters.

13. A system comprising:
a network communication interface to receive healthcare studies;
a memory coupled to the network communication interface to store received healthcare studies;
a display screen coupled to the memory to display the received healthcare studies; and
one or more processors coupled to the network connection interface, the memory and the display screen and configured to:
obtain healthcare studies, wherein the healthcare studies comprise one or more unread healthcare study and one or more read healthcare study, wherein each read healthcare study was assigned a priority level by a medical user;
access user-specified configuration information for configuring a first user interface of a medical management system, wherein the user-specified configuration information comprises one or more keywords, wherein the one or more keywords each comprise textual findings provided by an automated image analysis algorithm, wherein the image analysis algorithm previously automatically identified the textual findings in one or more images in one or more unread healthcare studies by performing an automated image analysis, the first user interface to display a list of the healthcare studies;
determine priority information for the healthcare studies in the list, according to the user-specified configuration information, wherein the determining comprises:
for each unread healthcare study of the one or more unread healthcare studies, assign a priority level to one or more images of a series of images comprising the unread healthcare study, according to the user-specified configuration information, based on performing the automated image analysis on the series of images in the unread healthcare study, wherein the automated image analysis comprises utilizing an image analysis algorithm to perform a textual analysis to locate the one or more keywords in the one or more images of the series of images, wherein the user-specified configuration information comprises pre-defined priority levels for images comprising each keyword of the one or more keywords and not comprising any keyword of the one or more keywords; and
for each read healthcare study of the one or more read healthcare studies, according to the user-specified configuration information, obtain the priority level assigned by the medical user;
create the first user interface with the list of the healthcare studies with the priority information comprising the priority levels of the one or more read healthcare studies and the one or more unread healthcare studies, based on the determining;

display the first user interface with the list of healthcare studies with the priority information on the display screen; and send an automated alert that is independent of the first user interface and responsive to one or more of the findings from the automated image analysis, wherein the user-specified configuration information indicates that the automated alert is to be sent in response to a predetermined finding in the results of automated image analysis performed one or more image of a healthcare study, and wherein at least one processor of the one or more processors is further operable to send, via the network communication interface, the alert to one or more predetermined healthcare providers responsible for handling a condition associated with the predetermined finding, and wherein the automated alert comprises the one or more keywords.

14. The system defined in claim 13, wherein at least one processor of the one or more processors is further operable to:

display a second user interface on the display screen associated with the medical image management system, the second user interface to receive user inputs specifying a priority level for results of an automated image analysis algorithm;

cause the capture of user input information from at least one user input made while a user engages with user interface elements of the second user interface, wherein the second user interface is responsive to user inputs to set priority of a healthcare study based on one or both of a numerical value and the one or more keywords; and create the user-specified configuration information based on the user input information, wherein if the user sets the priority based on both the numerical value and the one or more keywords, a priority associated with the one or more keywords is displayed as the priority for the healthcare study.

15. The system defined in claim 14, wherein the second user interface is operable to receive user input to set a priority level for findings of automated image analysis algorithms on a per automated image analysis algorithm basis.

16. The system defined in claim 14, wherein the numerical value comprises an abnormality score.

17. The system defined in claim 14, wherein the second user interface allows a user to specify a range for the numerical value associated with a priority level.

18. The system defined in claim 13, wherein the priority information indicates whether automated image analysis was performed on at least one image in each healthcare study and, if image analysis was performed, one or more of findings exist and contain one or more keywords specified via the user interface, findings exist but do not contain one or more keywords specified via the user interface, findings exist but no text is contained in the findings, and no findings exist.

19. The system of claim 13, wherein the text comprising each of the one or more keywords consists of a word consisting of letters.

20. A non-transitory computer readable storage media having instructions stored thereupon which, when executed by a system having at least a processor, a memory and a display screen therein, cause the system to perform a method comprising:

obtaining healthcare studies, wherein the healthcare studies comprise one or more unread healthcare study and one or more read healthcare study, wherein each read healthcare study was assigned a priority level by a medical user;

accessing user-specified configuration information for configuring a first user interface of a medical management system, wherein the user-specified configuration information comprises one or more keywords, wherein the one or more keywords each comprise textual findings provided by an automated image analysis algorithm, wherein the image analysis algorithm previously automatically identified the textual findings in one or more images in one or more unread healthcare studies by performing an automated image analysis, the first user interface to display a list of the healthcare studies;

determining priority information for the healthcare studies in the list, according to the user-specified configuration information, wherein the determining comprises:

for each unread healthcare study of the one or more unread healthcare studies, assigning a priority level to one or more images of a series of images comprising the unread healthcare study, according to the user-specified configuration information, based on performing the automated image analysis on the series of images in the unread healthcare study, wherein the automated image analysis comprises utilizing an image analysis algorithm to perform a textual analysis to locate the one or more keywords in the one or more images of the series of images, wherein the user-specified configuration information comprises pre-defined priority levels for images comprising each keyword of the one or more keywords and not comprising any keyword of the one or more keywords; and for each read healthcare study of the one or more read healthcare studies, according to the user-specified configuration information, obtaining the priority level assigned by the medical user;

creating the first user interface with the list of the healthcare studies with the priority information comprising the priority levels of the one or more read healthcare studies and the one or more unread healthcare studies, based on the determining;

displaying the first user interface with the list of healthcare studies with the priority information on the display screen of medical image management system; and sending an automated alert, responsive to one or more of the findings from the automated image analysis, independent of the displaying the first user interface, wherein the user-specified configuration information indicates that the automated alert is to be sent in response to a predetermined finding in the results of automated image analysis performed on one or more image of a healthcare study, wherein the sending comprises sending the automated alert to one or more predetermined healthcare providers responsible for handling a condition associated with the predetermined finding, and wherein the automated alert comprises the one or more keywords.

21. The computer readable storage media defined in claim 20, wherein the method further comprises:

displaying a second user interface on a display screen associated with the medical image management system, the second user interface to receive user inputs specifying a priority level for results of an automated image analysis algorithm;

capturing user input information from at least one user input made while a user engages with user interface elements of the second user interface, wherein the second user interface is responsive to user inputs to set priority of a healthcare study based on one or both of a numerical value and the one or more keywords; and creating the user-specified configuration information based on the user input information, wherein if the user sets the priority based on both the numerical value and the one or more keywords, a priority associated with the one or more keywords is displayed as the priority for the healthcare study.

22. The computer readable storage media defined in claim 21, wherein the second user interface is operable to receive user input to set a priority level for findings of automated image analysis algorithms on a per automated image analysis algorithm basis.

23. The computer readable storage media defined in claim 21, wherein the numerical value comprises an abnormality score.

24. The computer readable storage media defined in claim 21, wherein the second user interface allows a user to specify a range for the numerical value associated with a priority level.

25. The computer readable storage media defined in claim 20, wherein the priority information indicates whether automated image analysis was performed on at least one image in each healthcare study and, if image analysis was performed, one or more of
findings exist and contain one or more keywords specified via the user interface,
findings exist but do not contain one or more keywords specified via the user interface,
findings exist but no text is contained in the findings, and no findings exist.

26. The computer readable storage media of claim 20, wherein the text comprising each of the one or more keywords consists of a word consisting of letters.

* * * * *